(12) United States Patent
Warnking

(10) Patent No.: US 11,278,313 B2
(45) Date of Patent: Mar. 22, 2022

(54) TRANSEPTAL PUNCTURE PROCEDURE

(71) Applicant: AerWave Medical, Inc., Naples, FL (US)

(72) Inventor: Reinhard J. Warnking, Westlake, FL (US)

(73) Assignee: AERWAVE MEDICAL, INC., Naples, FL (US)

( * ) Notice: Subject to any disclaimer, the term of this patent is extended or adjusted under 35 U.S.C. 154(b) by 0 days.

(21) Appl. No.: 17/180,082

(22) Filed: Feb. 19, 2021

(65) Prior Publication Data

US 2021/0267627 A1 Sep. 2, 2021

Related U.S. Application Data

(60) Provisional application No. 62/980,775, filed on Feb. 24, 2020.

(51) Int. Cl.
| | |
|---|---|
| A61B 17/34 | (2006.01) |
| A61B 8/06 | (2006.01) |
| A61B 8/08 | (2006.01) |
| A61B 8/00 | (2006.01) |
| A61B 17/00 | (2006.01) |
| A61B 8/12 | (2006.01) |
| A61B 90/00 | (2016.01) |

(52) U.S. Cl.
CPC ............ *A61B 17/3403* (2013.01); *A61B 8/06* (2013.01); *A61B 8/0883* (2013.01); *A61B 8/12* (2013.01); *A61B 8/4494* (2013.01); *A61B 8/488* (2013.01); *A61B 17/00234* (2013.01); *A61B 2017/00243* (2013.01); *A61B 2017/3413* (2013.01); *A61B 2090/378* (2016.02); *A61B 2090/3784* (2016.02)

(58) Field of Classification Search
CPC .............. A61B 5/6848; A61B 17/3403; A61B 17/00234; A61B 8/06; A61B 8/0883; A61B 8/4494; A61B 8/488; A61B 2017/00243; A61B 2017/3413
USPC ......................................................... 600/461
See application file for complete search history.

(56) References Cited

U.S. PATENT DOCUMENTS

| | | | |
|---|---|---|---|
| 2003/0078645 A1* | 4/2003 | Pigott ................. | A61B 5/1459 607/122 |
| 2003/0191392 A1* | 10/2003 | Haldeman ............... | A61B 8/06 600/467 |
| 2017/0014159 A1* | 1/2017 | Stokes ................ | A61B 5/0044 |

* cited by examiner

*Primary Examiner* — Amelie R Davis
*Assistant Examiner* — John Denny Li
(74) *Attorney, Agent, or Firm* — R. Neil Sudol; Henry D. Coleman

(57) ABSTRACT

An apparatus and methods for transeptal punctures provide audible feedback to an operator or clinician with information to identify an intended needle or instrument pathway. Despite improved safety and simplification of the TSP itself, the apparatus enables the operator to optimize a crossing angle for various procedures, including PV isolation, valve repair, and appendage closure.

15 Claims, 2 Drawing Sheets

TRANSEPTAL PUNCTURE PROCEDURE

BACKGROUND OF THE INVENTION

The present invention relates to a medical transeptal crossing procedure.

The two upper chambers of the heart, the right and left atrium, are separated by the atrial septum. Transeptal punctures are becoming increasingly important with the realization of minimal invasive catheter based cardiac procedures. Mitral Valve repair, AF ablations and appendage closure all typically require a transeptal puncture. The puncture is being performed by crossing the intra atrial septum from the right atrium into the left atrium. This way the catheter traverses from the venous side to the arterial side. By entering the patient body through the venous side larger catheters can be utilized while minimizing the complication rate.

As disclosed by Hansen Medical in U.S. Pat. No. 7,753,853 (The '853 patent) a physiological parameter can be utilized to guide a transeptal puncture. However, as described in the '853 patent the septum must be at least partially traversed in order to detect a change of the physiologic parameter. The interventionalist typically accesses the left atrium by piercing the septum with a special needle, the Brockenbrough needle, under angiographic and often TEE guidance. This needle is hollow and enables detection of the blood pressure at the tip of the needle. Since right venous- and left atrial pressures are significantly different in value and flow pattern, the physician gets a visual confirmation that he has successfully accessed the left atrium by monitoring the pressure curves. However, this control mechanism is somewhat "after the fact" by confirming the needle position only, once the needle has entered the left atrium and is exposed to the higher blood pressure and arterial flow pattern. Even in experienced hands it does happen that the septum is punctured in the wrong location and or direction and structures like the aorta or the pericardium are penetrated, resulting in serious injury to the patient. While ICE (Intra Cardiac Echocardiography) or TEE (Trans Esophageal Echocardiography) imaging increases the safety of the transeptal puncture, such imaging is costly and time consuming. What would be desirable would be a simple method and apparatus to indicate the optimal needle position before the septum is partially or fully penetrated, without the use of additional imaging instrumentation.

SUMMARY OF THE INVENTION

Pursuant to the present invention, the above-mentioned procedural difficulties, with a change of the physiological parameter only after septal crossing, are addressed by utilizing a Doppler signal which detects left atrial blood flow without crossing, piercing or partially penetrating the septum. Preferably, one utilizes a pulsed Doppler approach to detect the left atrial blood flow characteristics through the septum, that is, from the right atrium, without a partial or complete crossing of the septum to ascertain a change of a physiological parameter. The left atrial flow pattern is detected through the septum without crossing or piercing the same. The amplitude of the Doppler signal will reach a maximum when the needle tip with the Doppler transceiver (Tx) is located adjacent to the fossa ovalis. In this way a safe transeptal crossing procedure is accomplished by ensuring that the needle points into the left atrium and is positioned at the thinnest portion of the septum (the fossa ovalis).

Pursuant to a further feature of the present invention, the depth and width of a Doppler sample volume is pre-selectable so that analysis of reflected ultrasound waves can detect not only left atrial blood flow and exclude accidentally penetrating neighboring structures like aorta or pericardium but can identify certain target areas such as a Pulmonary Vein in the case of PV isolation procedures or the mitral valve in case of MV repair or replacement. In this way not only a safe septal crossing is ensured but an optimal crossing angle to reach the target area can be determined.

Pursuant to an additional aspect of the invention, an ultrasound monitoring apparatus provides acoustic feedback to the clinician performing the transeptal puncture, facilitating the procedure since visual control or feedback is already overwhelming for the operator. Angiography, blood pressure, EKG, ICE, mapping of catheter position and catheter force all rely on visual displays. Therefore, the current invention preferably utilizes audio control to guide the transeptal puncture. The apparatus according to this aspect of the invention preferably includes an ultrasound transducer at the distal tip of a 14/1000 guidewire connected to a Doppler system operating in pulsed Doppler mode. (See, for example, products of Volcano Corp.)

As disclosed by Hansen Medical, a physiological parameter can be utilized to guide a transeptal puncture. However, as set forth in the '853 patent the septum needs to be at least partially traversed in order to detect a change of the physiologic parameter.

Unlike the device described in the '853 patent, an apparatus pursuant to the current invention does not require specialized equipment (14/1000 needle and wire with integrated sensor) for the transeptal puncture. A standard Brockenbrough needle can be utilized. Doppler guidance is achieved by advancing a flow wire (for example, of Volcano Corp.) through the standard hollow Brockenbrough needle.

Another application of the present invention enables coronary sinus access. A flow wire is introduced through a steerable sheath until the Doppler Tx reaches the distal opening of the sheath and an associated audible Doppler signal indicates significant venous flow towards the ultrasound transducer when the coronary sinus opening has been identified. Typically, a catheter is then advanced into the coronary sinus after the flow wire has been withdrawn. Other applications would be PFO (Patent Foramen Ovale) closure and appendage closure. In the case of PFO closure, again, a significant Doppler signal towards the transducer enables identification of the location of the repair site, while in the case of appendage closure an absence of a flow signal (or a chaotic flow pattern) confirms correct positioning.

An apparatus for enabling safe transeptal punctures, comprises a hollow needle, a flow wire or guidewire with a distal ultrasound transceiver (Tx) disposed in the lumen of the hollow needle, and a waveform generator operatively connected to the ultrasound transducer and configured to energize the ultrasound transducer to produce a pulsed ultrasound pressure wave of predetermined duration. A signal receiver is operatively connected to the ultrasound transducer, while a signal processor is operatively connected to the receiver and a storage medium such as an electronic storage unit. The signal processor is configured to record, in the storage medium, magnitudes of Doppler frequency changes of ultrasonic waves reflected from one or more predetermined sample volumes at respective predetermined distances from the ultrasound transducer in a selected ultrasound-transmissive medium.

Preferably, the apparatus further comprises an electroacoustic transducer operatively connected to the signal processor to generate an audible signal varying with Doppler magnitude as dependent on a direction of propagation of the pulsed ultrasound pressure wave in the selected ultrasound-transmissive medium.

The waveform generator may be operatively connected to the signal processor for transmitting to the ultrasound transducer, in response to a control signal from the signal processor, a pulsed electrical signal inducing the ultrasound transducer to produce the pulsed ultrasound pressure wave of the predetermined duration. The signal receiver and the signal processor are configured to process Doppler frequency changes of incoming reflected pressure waves arriving at a predetermined interval after termination of the pulsed ultrasound pressure wave, whereby size and location of the predetermined sample volume may be preselected.

The apparatus may additionally comprising means such as a sheath for steering or orienting a distal end portion of the hollow needle and/or the Doppler flow wire to thereby adjust a direction of propagation of the pulsed ultrasound pressure wave and at least partially locations of the sample volumes.

The needle and (or) the flow wire are inserted through a lumen of the steerable sheath, thereby enabling accessing of a target structure in accordance with an audible Doppler flow signal produced by the electro-acoustic transducer.

The steerability of the sheath and the flow wire enables a precise location for the placement of a PFO closure device in accordance with an audible Doppler flow signal produced by the electro-acoustic transducer. In this application the sample volume depth is chosen to be a few mm's.

The predetermined sample volume typically has a depth of several centimeters, chosen so that not only left atrial blood flow is detectable but certain target areas can be identified, the target areas including Pulmonary Veins for PV isolation procedures and the mitral valve for MV repair or replacement, and the appendage in case of appendage closures. Also, structures to be avoided, particularly the Aorta, can be identified and a safe needle path can be chosen to avoid puncturing these structures.

An apparatus for enabling safe transeptal punctures comprises, in accordance with the present invention, a hollow needle, a flow wire or guidewire disposed in a lumen of the hollow needle, an ultrasound transducer mounted to a distal end portion of the flow wire or guidewire, and a waveform generator operatively connected to the ultrasound transducer and configured to energize the ultrasound transducer to produce a pulsed ultrasound pressure wave of predetermined duration. The apparatus further comprises a signal receiver operatively connected to the ultrasound transducer, an electronic storage unit, and a signal processor operatively connected to the waveform generator, the signal receiver and the electronic storage unit. The signal processor is configured to activate the signal receiver to commence detecting incoming ultrasonic pressure waves a predetermined interval after the waveform generator terminates energization of the ultrasound transducer and production of the pulsed ultrasound pressure wave. The signal processor is further configured to record in the electronic storage unit magnitudes of Doppler frequency changes of ultrasonic waves reflected from one or more predetermined sample volumes at respective predetermined distances from the ultrasound transducer in a selected ultrasound-transmissive medium. An electro-acoustic transducer is connected to the signal processor for generating, in response to signals therefrom, an audible signal varying with Doppler frequency shift magnitude in accordance with direction of propagation of the pulsed ultrasonic pressure wave from the ultrasound transducer into the left atrium so safe septal crossing is ensured and an optimal crossing angle to reach the target area can be determined.

Pursuant to another feature of the invention, the waveform generator is operatively connected to the signal processor for transmitting to the ultrasound transducer, in response to a control signal from the signal processor, a pulsed electrical signal inducing the ultrasound transducer to produce the pulsed ultrasound pressure wave of the predetermined duration, while the signal receiver and the signal processor are configured to process Doppler frequency changes of incoming reflected pressure waves arriving a predetermined interval after termination of the pulsed ultrasound pressure wave, whereby size and location of the predetermined sample volume may be preselected.

In accordance with a further feature of the invention, the signal processor and the electronic storage unit are configured for recording a pulsed Doppler signal generated at least several millimeters distal to a puncture tip of the hollow needle across the septum in the left atrium.

In a preferred embodiment of the present invention, the apparatus further comprises a steerable sheath. The flow wire or guidewire and the hollow needle are inserted through a lumen of the steerable sheath, thereby enabling (a) adjustment in a direction of propagation of the pulsed ultrasound pressure wave and at least partially locations of the sample volumes, (b) directing the needle pathway towards a target structure in accordance with an audible Doppler flow signal produced by the electro-acoustic transducer, and (c) determination of any of a plurality of precise locations in the left atrium for (i) pulmonary vein isolation procedures, (ii) mitral valve repair or replacement, (iv) appendage closures, and (iv) the placement of a PFO closure device in accordance with an audible Doppler flow signal produced by the electro-acoustic transducer.

A medical method in accordance with the present invention comprises inserting a distal end portion of a steerable sheath into a vascular system of a mammalian subject, and advancing the sheath through the vascular system of the mammalian subject so that the distal end portion is located in a right atrium of the mammalian subject, where a hollow needle with an ultrasound transducer at a distal end of the hollow needle is disposed in a lumen of the sheath. The method additionally comprises manipulating the steerable sheath, the hollow needle and the ultrasound transducer to position the ultrasound transducer in the right atrium within effective ultrasound transmission distance of a cardiac septum of the mammalian subject and so that a sharp distal tip of the hollow needle is spaced from a cardiac septum of the mammalian subject. Thereafter the ultrasound transducer is actuated to emit a pulsed ultrasonic pressure wave of predetermined duration, The method also comprises, monitoring incoming reflected pressure waves after a predetermined interval after termination of the pulsed ultrasonic pressure wave, calculating blood flow velocities from frequency shifts of the incoming reflected pressure waves, and operating an electro-acoustic transducer to generate an audible signal varying with Doppler frequency shift magnitude in accordance with direction of propagation and location at the fossa ovalis of the pulsed pressure wave from the ultrasound transducer into the left atrium.

The monitoring of the incoming reflected pressure waves may include detecting the incoming reflected ultrasound waves via the ultrasound transducer, the method further comprising controlling timing parameters of the pulsed ultrasonic pressure wave and of the monitoring of the incoming reflected pressure waves to ascertain blood flow velocity within a predetermined sample volume within the left atrium. The actuating of the ultrasound transducer includes energizing same to emit the pulsed ultrasonic pressure wave as a series of ultrasonic pressure wave pulses having a combined duration predetermined to provide the predetermined sample volume with a preselected length. The monitoring the incoming reflected pressure waves via the ultrasound transducer after the predetermined time interval serves to locate the sample volume at a predetermined distance from the ultrasound transducer in the left atrium of the mammalian subject.

Where the ultrasound transducer is attached to a distal end of a wire, providing the hollow needle with the ultrasound transducer includes inserting a distal end portion of the wire into a lumen of the hollow needle.

The actuating of the ultrasound transducer generally includes detecting reflected ultrasound waves via the ultrasound transducer, the method further comprising manipulating the hollow needle to move the distal end portion thereof through the cardiac septum in a direction determined in accordance with characteristics of the reflected ultrasound waves.

The method may further comprising steering the sheath to orient the distal end portion thereof in a desired direction towards an extremum of the audible signal and thereafter shifting the hollow needle distally through the steerable sheath and into the cardiac septum of the mammalian subject in the desired direction.

The method may further comprise accessing a coronary sinus in the right atrium in accordance with an audible Doppler flow signal produced by the electro-acoustic transducer.

A method for crossing a cardiac septum in a mammalian subject comprises, in accordance with the present invention, (i) providing a flow wire having a Doppler ultrasound transducer at a distal end thereof, (ii) inserting a distal end portion of the flow wire into a lumen of a hollow needle, (iii) advancing the hollow needle through a steerable sheath so that a distal end portion of the needle is located in a right atrium of the mammalian subject and so that the distal end portion of the needle is spaced from the cardiac septum without penetrating into the cardiac septum, (iv) manipulating the hollow needle and the flow wire to position the Doppler ultrasound transducer in the right atrium and facing towards the septum of the mammalian subject while that the distal end portion of the needle is spaced from the cardiac septum and does not penetrate into the cardiac septum, and (v) thereafter actuating the Doppler transducer to transmit pulsed Doppler signals to scan blood flow velocity within a predetermined sample volume located transeptally in a left atrium of the mammalian subject.

The actuating of the Doppler transducer typically includes inducing the Doppler transducer to produce a pulsed ultrasound pressure wave of a predetermined duration. The method further comprises (vi) monitoring incoming reflected pressure waves arriving a predetermined interval after termination of the pulsed ultrasound pressure wave, whereby size and location of the predetermined sample volume may be preselected to be located within the left atrium of the mammalian subject, and (vii) inserting the distal end portion of the hollow needle into the cardiac septum only after detection of blood flow velocity of a predetermined desired characteristic.

The method may further comprise steering or orienting a distal end portion of the flow wire to thereby adjust a direction of propagation of the pulsed ultrasound pressure wave and at least partially location of the sample volume.

Pursuant to further features of the invention, one inserts the hollow needle and the flow wire through a lumen of a steerable sheath and steers or orients the distal end portion of the flow wire b adjusting an orientation direction of a distal end of the steerable sheath, the inserting of the distal end portion of the hollow needle into the cardiac septum being in a direction controlled by adjusting the orientation of the distal end of the steerable sheath The method preferably further comprises activating an electro-acoustic transducer to generate an audible signal varying with Doppler frequency shift magnitude in accordance with direction of propagation of the pulsed ultrasonic pressure wave from the ultrasound transducer into the left atrium and performing a surgical procedure taken from the group consisting of (i) pulmonary vein isolation procedures, (ii) mitral valve repair or replacement, (iv) appendage closures, and (iv) the placement of a PFO closure device, all carried out in accordance with an audible Doppler flow signal produced by the electro-acoustic transducer.

DETAILED DESCRIPTION

Figure 1:
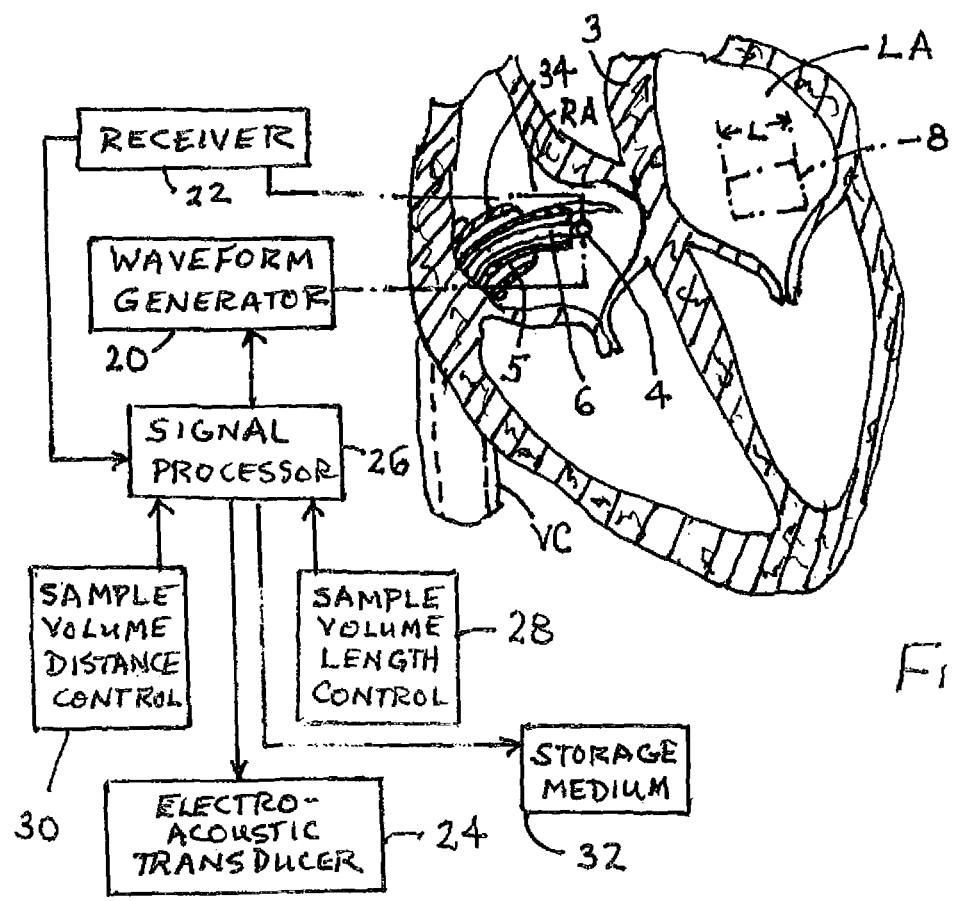
FIG. 1 is a diagram of a distal end portion of a Brockenbrough needle with a flow wire advanced through its lumen, placed at an intra-atrial cardiac septum before a crossing or penetration of the septum.

As depicted in FIG. 1, an apparatus according to one embodiment of the invention includes a flow wire or guidewire with a Doppler transducer mounted to the distal tip 6 inserted through a hollow needle 5. Flow wire or guidewire 6 may be a 14/1000 guidewire, with an ultrasound transducer 4 being located at the tip of the 14/1000 guidewire.

Figure 2:
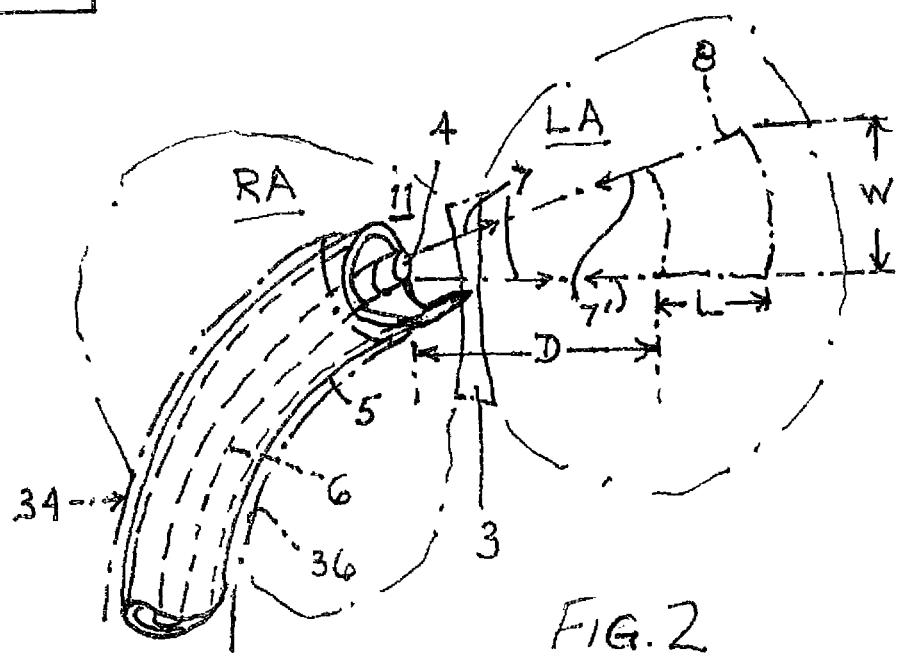
FIG. 2 is a diagram showing a Pulsed Doppler transmit signal, gating time and a resulting position and size of a sample volume.

The flow wire 6 utilizes a pulsed Doppler principle (FIG. 2). A waveform generator 20 transmits a pulsed ultrasonic electrical signal to transducer 4, energizing the transducer to emit a burst of pulses of one or more ultrasonic frequencies. The burst length, that is, the number of pulses multiplied by the pulse duration, determines the length L of the sample volume 8 while the gating time (interval between end of pulse burst and time when the apparatus switches waveform generator 20 off and switches a receiver 22 on) determines the depth D of the sample volume 8 or distance of the sample volume to the transducer 4. Once the tip of the needle 5 with the flow wire-transducer 4 is positioned in the right atrium RA at the cardiac or intra-atrial septum 3 the sample volume 8 is located in the left atrium LA, on the other side of the septum 3. Therewith, a Doppler audio signal produced by a transducer or speaker 24 in response to a signal from a control unit 26 at an output of receiver 22 represents or signals a magnitude and flow pattern of left atrial blood flow without the needle 5 having crossed or even partially penetrated the septum 3. With needle 5 properly positioned so that the audio signal clearly represents maximal left atrial blood flow because of minimal absorption and thus identifies the fossa ovalis position 11, the needle can be safely advanced across the septum 3.

In response to a control signal from processor 26, waveform generator 20 transmits an energization signal to transducer 4 inducing the transducer to emit a pulsed ultrasound pressure wave 7 of predetermined duration. The duration determines the length L of sample volume 8. The pulse train duration may be selectively adjusted by an operator via a sample-volume length control 28. A width W of any given sample volume 8 is determined by the transducer beam geometry.

Signal receiver 22 and signal processor 26 are further configured to process Doppler frequency changes of incoming reflected pressure waves 7' arriving a predetermined time after termination of a pulsed ultrasound pressure wave output by transducer 4, so that distance or range of sample volume 8 may be selected in addition to length (L) and angular location (azimuth and elevation) of the sample volume. An operator may modify the distance or range D of sample volume 8 from transducer 4 by a sample-volume distance control 30 operatively connected to signal processor 26.

Figure 3:
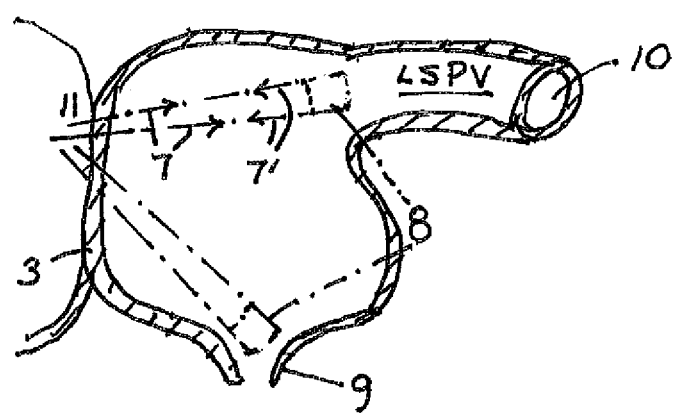
FIG. 3 is a diagram illustrating use of a pulsed Doppler sample volume to identify a LSPV (10) and a Mitral Valve (9) and optimized needle paths (7, 7') to reach these target areas.

Further the depth D of the Doppler sample volume 8 in FIG. 3 can be chosen so that not only left atrial blood flow is detected but certain target areas can be identified such as Pulmonary Veins (for example the LSPV) 10 in the case of PV isolation procedures or the mitral valve 9 in case of MV repair or replacement. Thus not only is a safe septal crossing ensured but also the optimal crossing angle to reach the target area is determined.

Signal processor 26 may be operatively connected to an electronic storage unit or other storage medium 32, to record therein magnitudes of Doppler frequency changes of ultrasonic waves reflected from one or more predetermined sample volumes 8 at respective predetermined distances D (e.g., at least several millimeters) from the ultrasound transducer 4 in a selected ultrasound-transmissive medium such as the blood and heart tissues of a mammalian subject.

As depicted in FIG. 2, hollow needle 5 preferably extends longitudinally through a lumen 34 of a steerable sheath 36 that enables an operator to steer or orient a distal end portion (not separately designate) of the needle to thereby adjust a direction of propagation of the pulsed ultrasound pressure wave 7 emitted by transducer 4. This orientation control allows adjustability of the azimuth and elevations of sample volume 8, in addition to enabling accessing of a target structure (e.g., cardiac structure) in accordance with an audible Doppler flow signal produced by electro-acoustic transducer 24.

The ability to control orientation of the distal end of needle 5 enables identification of target areas such as Left Superior Pulmonary Vein (LSPV) 10 (FIG. 3) for PV isolation procedures and mitral valve (MV) 9 for repair or replacement thereof, and the appendage in case of appendage closures. Moreover, a precise location may be determined for the placement of a PFO closure device in accordance with an audible Doppler flow signal produced by the electro-acoustic transducer 24.

In a medical method as illustrated in the drawings, a distal end portion of needle 5 is inserted through a sheath into a vascular system of a mammalian subject, and advanced through the vascular system, typically through the vena cava VC so that the distal end portion of the needle is located in the right atrium RA of the subject. An interventional cardiologist or other operator manipulates needle 5, typically by steering or maneuvering sheath 36 together with needle 5 and transducer 4 therein, to position transducer 4 in right atrium RA within effective ultrasound transmission distance of cardiac or intra-atrial septum 3. Transducer 4 is activated to emit pulsed ultrasonic pressure waves configured to monitor blood flow velocities via frequency shifts of return ultrasonic waves reflected at least in part from moving blood in sample volume 8 inside left atrium LA of the subject. Preferably, electro-acoustic transducer 24 is operated to generate an audible signal varying with Doppler frequency shift and magnitude in accordance with direction of propagation of the pulsed ultrasound pressure waves 7 from ultrasound transducer 4 into left atrium LA.

The actuating of ultrasound transducer 4 during a Doppler procedure entails detecting reflected ultrasound waves 7' via the transducer, controlling timing parameters of the emitted pulsed pressure waves 7 and the detecting of the reflected ultrasound waves 7' to monitor blood flow velocity within sample volume 8 within left atrium LA.

The actuating of ultrasound transducer 4 further entails energizing the transducer to emit a series of ultrasonic pressure wave pulses 7 having a combined duration predetermined to provide sample volume 8 with length L.

In addition, the method comprises detecting the reflected ultrasound waves 7' via transducer 4 after a predetermined time lag or delay after a termination of the series of ultrasonic pressure wave pulses 7, whereby the sample volume 8 is located at a predetermined distance D or range from transducer 4 in left atrium LA.

Wire 6 with ultrasound transducer 4 at the distal end thereof may be inserted into needle 5 after arrival of the distal end portion thereof in right atrium RA. However, wire 6 and needle 5 may be disposed inside sheath 36 during the insertion thereof through the vascular system of the subject.

It is contemplated that the medical method further comprises manipulating needle 5, optimally by steering sheath 36, to move the distal end portion of the needle through the cardiac septum 3 in a direction determined in accordance with characteristics of the reflected ultrasound waves 7'.

In an additional method, an operator orients a distal end portion (not labeled) of sheath 36 within the right atrium to orient same in a desired direction towards an extremum (maximum) of the audible signal produced by transducer 24, shifts the steerable sheath 36 in the desired direction and advances a catheter. In this way, one may access a coronary sinus in the right atrium.

It is to be noted that needle 5 is used only for transeptal punctures (TSPs) and not for pulmonary vein (PV) isolation or coronary sinus access.

The present invention provides a technique for obtaining an optimal sheath position to perform various conventional procedures, both in the right atrium alone and transeptally in the left atrium. In a PFO closure, one deploys an "umbrella" device in a septum and opens or expands closure elements on opposite sides of the septum in order to close a leak. This procedure is typically done from the right atrium. In this case needle 5 is not required at all since one does not require separate access to the left atrial side. The Doppler apparatus disclosed herein locates the leak and the sheath is positioned next to the hole and the closure device advanced into the hole.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A medical method, comprising:
    inserting a distal end portion of a steerable sheath into a vascular system of a mammalian subject;

advancing said sheath through the vascular system of the mammalian subject so that said distal end portion is located in a right atrium of the mammalian subject, an ultrasound transducer being disposed in a lumen of said sheath and in said distal end portion;

manipulating said steerable sheath to position said ultrasound transducer in said right atrium within effective ultrasound transmission distance of a fossa ovalis of a cardiac septum of the mammalian subject;

thereafter actuating said ultrasound transducer to emit a pulsed ultrasonic pressure wave of predetermined duration through said cardiac septum at said fossa ovalis and into a left atrium of the mammalian subject;

beginning a predetermined interval after termination of said pulsed ultrasonic pressure wave, monitoring incoming reflected pressure waves emanating from said left atrium of the mammalian subject and received by said ultrasound transducer via said fossa ovalis;

calculating blood flow velocities of blood in said left atrium from Doppler frequency shifts of the incoming reflected pressure waves relative to said pulsed ultrasonic pressure wave, the calculated blood flow velocities having values varying as a function of direction of propagation of said incoming reflected pressure waves; and operating an electro-acoustic transducer to generate an audible signal varying with Doppler frequency shift magnitude and calculated blood flow velocity and direction of propagation of said incoming reflected pressure waves.

2. The medical method of claim 1 wherein the monitoring of the incoming reflected pressure waves includes detecting the incoming reflected ultrasound waves via said ultrasound transducer, further comprising controlling timing parameters of the pulsed ultrasonic pressure wave and of the monitoring of the incoming reflected pressure waves to ascertain blood flow velocity within a predetermined sample volume within said left atrium, the actuating of said ultrasound transducer includes energizing said ultrasound transducer to emit the pulsed ultrasonic pressure wave as a series of ultrasonic pressure wave pulses having a combined duration predetermined to provide said predetermined sample volume with a preselected length, the monitoring said incoming reflected pressure waves via said ultrasound transducer after the predetermined time interval serving to locate said predetermined sample volume at a predetermined distance from said ultrasound transducer.

3. The medical method of claim 1 wherein said ultrasound transducer is attached to a distal end of a wire, further comprising inserting a distal end portion of said wire into said lumen of said sheath.

4. The medical method of claim 1 wherein said ultrasound transducer is located at a distal end of a hollow needle inserted inside said lumen of said sheath and wherein the actuating of said ultrasound transducer includes detecting reflected ultrasound waves via said ultrasound transducer, further comprising manipulating said hollow needle to move said distal end portion thereof through said cardiac septum in a direction determined in accordance with blood flow velocities calculated from the reflected ultrasound waves.

5. The method defined in claim 1 wherein said ultrasound transducer is located at a distal end of a hollow needle inserted inside said lumen of said sheath, further comprising:

steering said sheath to orient the distal end portion thereof in a desired direction towards an extremum of said audible signal; and thereafter shifting said hollow needle distally through said steerable sheath and into the cardiac septum of the mammalian subject in the desired direction.

6. The medical method of claim 1, further comprising: accessing a coronary sinus in the right atrium in accordance with an audible Doppler flow signal produced by said electro-acoustic transducer.

7. A medical method, comprising:

providing a sheath having an ultrasound transducer disposed in a lumen of said sheath at a distal end thereof;

inserting said sheath so that the ultrasound transducer and a distal end portion of the sheath are located in a right atrium of a mammalian subject and so that the ultrasound transducer and the distal end portion of the sheath are spaced from a cardiac septum of the mammalian subject;

thereafter actuating the ultrasound transducer, while the same is disposed in the right atrium, to transmit pulsed ultrasound signals through the cardiac septum to scan a space located transeptally in a left atrium of the mammalian subject;

operating said ultrasound transducer to receive reflected ultrasound waves from said space and convert said reflected ultrasound waves into electrical signals characterized by one or more ultrasonic frequencies; and subsequently processing said electrical signals from the ultrasound transducer to detect, through the cardiac septum without crossing, piercing or partially penetrating the cardiac septum, left atrial blood flow, the processing of said electrical signals from the ultrasound transducer including determining a maximum amplitude of the reflected ultrasound waves as a function of location of the ultrasound transducer along the cardiac septum, the maximum amplitude occurring when the sheath with a transceiver is located adjacent to the fossa ovalis of the cardiac septum, thereby enabling determination of the location of the fossa ovalis.

8. The method defined in claim 7, further comprising:

providing a flow wire having the ultrasound transducer mounted to a distal end thereof, a leading end portion of said flow wire being disposed in said lumen of said sheath;

manipulating the sheath and the flow wire to position the ultrasound transducer in said right atrium and facing towards the cardiac septum while the distal end portion of said sheath is spaced from the cardiac septum;

thereafter actuating the ultrasound transducer, while the same is disposed in the right atrium, to transmit pulsed ultrasound waves through the cardiac septum; and steering or orienting the leading end portion of the flow wire to thereby adjust a direction of propagation of the pulsed ultrasound waves and at least partially location of a sample volume.

9. The method of claim 8 wherein the steering or orienting of the leading end portion of the flow wire includes adjusting an orientation direction of a distal end of the steerable sheath.

10. The method of claim 8, further comprising:

activating an electro-acoustic transducer to generate an audible signal varying with a Doppler frequency shift magnitude in accordance with direction of propagation of said pulsed ultrasonic pressure wave from the ultrasound transducer into said left atrium; and performing a surgical procedure taken from the group consisting of (i) pulmonary vein isolation procedures, (ii) mitral valve repair or replacement, (iii) appendage closures, and (iv) the placement of a PFO closure device, all carried out in accordance with an audible Doppler flow signal produced by said electro-acoustic transducer.

11. The method of claim 7 wherein the actuating of the ultrasound transducer includes inducing the ultrasound transducer to produce a pulsed ultrasound pressure wave of a predetermined duration, further comprising monitoring incoming reflected pressure waves arriving a predetermined interval after termination of said pulsed ultrasound pressure wave, whereby size and location of a predetermined sample volume within said space may be preselected to be located within the left atrium of the mammalian subject.

12. A medical method conducted in a mammalian subject, comprising:
providing a wire having an ultrasound transducer disposed at a distal end thereof;
inserting said wire into the mammalian subject so that the ultrasound transducer is located in a right atrium of the mammalian subject spaced from a cardiac septum of the mammalian subject without penetrating into the cardiac septum;
thereafter actuating the ultrasound transducer, while the same is disposed in the right atrium, to transmit pulsed ultrasound waves through the cardiac septum to scan a volume located transeptally in a left atrium of the mammalian subject; and
processing reflected ultrasound waveforms to determine an area or point of the cardiac septum of minimal absorption of ultrasound energy by the cardiac septum and further to determine a location of a predetermined potential surgical treatment site in said left atrium by calculating blood flow velocities of blood in said left atrium from Doppler frequency shifts of the incoming reflected pressure waves relative to said pulsed ultrasonic waves, the calculated blood flow velocities having values varying as a function of direction of propagation of said incoming reflected pressure waves.

13. The method defined in claim 12, further comprising inserting the distal end portion of a needle from the right atrium of the mammalian subject through the cardiac septum along a linear path defined by (i) the area or point of minimal absorption and (ii) the location of the predetermined potential surgical treatment site.

14. The method defined in claim 12 wherein the area or point of minimal absorption is the fossa ovalis of the cardiac septum and wherein the predetermined potential surgical treatment site is selected for performing a surgical procedure taken from the group consisting of (i) pulmonary vein isolation procedures, (ii) mitral valve repair or replacement, (iii) appendage closures, and (iv) the placement of a PFO closure device.

15. The method defined in claim 12 wherein the processing of reflected ultrasound waveforms includes:
monitoring incoming reflected pressure waves emanating from said left atrium of the mammalian subject and received by said ultrasound transducer via said fossa ovalis; and
calculating blood flow velocities of blood in said left atrium from Doppler frequency shifts of the incoming reflected pressure waves relative to said pulsed ultrasonic pressure wave, the calculated blood flow velocities having values varying as a function of direction of propagation of said incoming reflected pressure waves.

* * * * *